(12) United States Patent
Wentorf

(10) Patent No.: US 9,877,838 B2
(45) Date of Patent: *Jan. 30, 2018

(54) TIBIAL BASEPLATES FOR SPECIAL PATIENT POPULATIONS

(71) Applicant: Zimmer, Inc., Warsaw, IN (US)

(72) Inventor: Mary S. S. Wentorf, Warsaw, IN (US)

(73) Assignee: Zimmer, Inc., Warsaw, IN (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/803,509

(22) Filed: Jul. 20, 2015

(65) Prior Publication Data

US 2015/0320565 A1  Nov. 12, 2015

Related U.S. Application Data

(63) Continuation of application No. 13/760,957, filed on Feb. 6, 2013, now Pat. No. 9,107,756.

(60) Provisional application No. 61/595,517, filed on Feb. 6, 2012.

(51) Int. Cl.
*A61F 2/38* (2006.01)
*A61F 2/30* (2006.01)

(52) U.S. Cl.
CPC .......... *A61F 2/389* (2013.01); *A61F 2/30942* (2013.01); *A61F 2002/30326* (2013.01); *A61F 2002/30616* (2013.01)

(58) Field of Classification Search
CPC ............ A61F 2/389; A61F 2002/30616; A61F 2002/30326
See application file for complete search history.

(56) References Cited

U.S. PATENT DOCUMENTS

| | | | |
|---|---|---|---|
| 5,271,737 A | 12/1993 | Baldwin et al. | |
| 5,344,460 A | 9/1994 | Turanyi et al. | |
| 5,613,970 A | 3/1997 | Houston et al. | |
| 8,568,486 B2 | 10/2013 | Wentorf et al. | |
| 9,107,756 B2 | 8/2015 | Wentorf | |
| 2011/0087332 A1 | 4/2011 | Bojarski et al. | |
| 2011/0251695 A1* | 10/2011 | Lenz | A61F 2/0811 623/20.15 |
| 2012/0022658 A1 | 1/2012 | Wentorf | |
| 2012/0022659 A1 | 1/2012 | Wentorf | |
| 2012/0022660 A1 | 1/2012 | Wentorf | |
| 2013/0204383 A1 | 8/2013 | Wentorf | |

OTHER PUBLICATIONS

"U.S. Appl. No. 13/760,957, Non Final Office Action dated Oct. 31, 2014", 13 pgs.
"U.S. Appl. No. 13/760,957, Notice of Allowance dated Apr. 17, 2015", 11 pgs.
"U.S. Appl. No. 13/760,957, Response filed Feb. 2, 2015 to Non-Final Office Action dated Oct. 31, 2014", 8 pgs.

(Continued)

*Primary Examiner* — David H Willse
*Assistant Examiner* — Javier Blanco
(74) *Attorney, Agent, or Firm* — Schwegman Lundberg & Woessner, P.A.

(57) ABSTRACT

A family of tibial baseplates can comprise a plurality of tibial baseplates. Each of the plurality of tibial baseplates can define a common nominal baseplate size and a unique, non-congruent tibial baseplate periphery as compared to the other tibial baseplates of the family of tibial baseplates.

4 Claims, 10 Drawing Sheets

(56) References Cited

OTHER PUBLICATIONS

"U.S. Appl. No. 13/760,957, Response filed Sep. 18, 2014 to Restriction Requirement dated Jul. 18, 2014", 7 pgs.
"U.S. Appl. No. 13/760,957, Restriction Requirement dated Jul. 18, 2014", 7 pgs.

* cited by examiner

TIBIAL BASEPLATES FOR SPECIAL PATIENT POPULATIONS

CLAIM OF PRIORITY

This application is a continuation of U.S. patent application Ser. No. 13/760,957, filed on 6 Feb. 2013, now issued as U.S. Pat. No. 9,107,756, which application claims the benefit of priority under 35 U.S.C. § 119(e) of U.S. Provisional Application Ser. No. 61/595,517, filed on 6 Feb. 2012, which applications are herein incorporated by reference in their entirety.

TECHNICAL FIELD

The present disclosure relates to orthopaedic prostheses and, specifically, to tibial baseplate components in a knee prosthesis.

BACKGROUND

Orthopaedic prostheses are commonly utilized to repair or replace damaged bone and tissue in the human body. For example, a knee prosthesis can include a tibial baseplate that is affixed to a resected or natural proximal tibia, a femoral component attached to a resected or natural distal femur, and a tibial bearing component coupled with the tibial baseplate and disposed between the tibial baseplate and femoral component. Knee prostheses frequently seek to provide articulation similar to a natural, anatomical articulation of a knee joint, including providing a wide range of flexion.

The tibial bearing component, also referred to as a tibial insert or meniscal component, can be used to provide an appropriate level of friction or contact area at the interface between the femoral component and the tibial baseplate. For a knee prosthesis to provide a sufficient range of flexion with a desirable kinematic motion profile, the tibial bearing component or tibial baseplate can be sized or oriented to interact appropriately with the femoral component of the knee prosthesis throughout the flexion range.

A given prosthetic component design, such as a tibial baseplate, tibial bearing component, or femoral component, can be provided to a surgeon as a kit including a variety of different sizes or prosthesis styles. During the surgical implantation procedure, such a kit can allow the surgeon to choose an appropriate component size or style on the basis of pre-surgery planning or intraoperative assessment of fit, such as how closely the component matches the natural contours of a patient's bone. Further, such a kit can allow the surgeon to choose an appropriate component size or style on the basis of kinematics, such as how smoothly the assembled knee joint prosthesis functions in conjunction with adjacent soft tissues and other anatomical structures. Soft tissue considerations can include proper ligament tension and minimization of soft tissue impingement upon prosthetic surfaces, for example.

In addition to prosthetic sizing, the orientation of a prosthetic component on a resected or natural surface of a bone can impact surgical outcomes. For example, the rotational orientation of a tibial baseplate and tibial bearing component with respect to a resected proximal tibia can affect the interaction between the corresponding femoral prosthesis and the tibial bearing component. The nature and amount of the coverage of a tibial baseplate over specific areas of the resected proximal tibia can also affect the fixation of the implant to the bone.

SUMMARY

The present inventor has recognized, among other things, that tibial baseplate peripheries can be altered to better fit special or unique patient populations. However, providing a unique tibial baseplate periphery can be costly or time prohibitive. One way to improve tibial baseplate fit is to classify resected proximal tibial peripheries into special patient populations and to design tibial baseplates for those populations.

To better illustrate the variable density implant and related methods disclosed herein, a non-limiting list of examples is provided here:

In Example 1, a family of tibial baseplates comprises a plurality of tibial baseplates, each of the plurality of tibial baseplates defining a common nominal baseplate size, each of the plurality of tibial baseplates defining a unique, non-congruent tibial baseplate periphery as compared to the other tibial baseplates of the family of tibial baseplates.

In Example 2, the family of tibial baseplates of Example 1 is optionally configured such that each of the plurality of baseplates comprises an anteroposterior axis configured to divide the tibial baseplate periphery into a medial compartment and a lateral compartment.

In Example 3, the family of tibial baseplates of any one or any combination of Examples 1-2 is optionally configured such that each of the plurality of tibial baseplates comprises an anterior edge; a lateral posterior edge generally opposite the anterior edge and forming a posterior boundary of the lateral compartment, the lateral compartment defining a lateral anteroposterior extent extending from the anterior edge of the tibial baseplate periphery to the lateral posterior edge thereof; and a medial posterior edge generally opposite the anterior edge and forming a posterior boundary of the medial compartment, the medial compartment defining a medial anteroposterior extent extending from the anterior edge of the tibial baseplate periphery to the medial posterior edge thereof, wherein the medial anteroposterior extent being larger than the lateral anteroposterior extent.

In Example 4, the family of tibial baseplates of any one or any combination of Examples 1-3, is optionally configured such that each of the plurality of tibial baseplates comprises a mediolateral extent defining the longest line segment within the tibial baseplate periphery.

In Example 5, the family of tibial baseplates of any one or any combination of Examples 1-4 is optionally configured such that each of the plurality of tibial baseplate peripheries is asymmetrical.

In Example 6, the family of tibial baseplates of any one or any combination of Examples 1-5 is optionally configured such that each of the plurality of baseplates comprises a posterior cruciate ligament (PCL) cutout area generally opposite an anterior edge and between the medial compartment and the lateral compartment.

In Example 7, the family of tibial baseplates of any one or any combination of Examples 1-6 is optionally configured such that the anteroposterior axis of each of the plurality of baseplates bisects the PCL cutout area.

In Example 8, the family of tibial baseplates of any one or any combination of Examples 1-7 is optionally configured such that an anteroposterior axis of each of the plurality of tibial baseplates is configured to be aligned with a home axis when mounted to a resected proximal tibia, the home axis defined as a line segment extending from a posterior point at a geometric center of an attachment area between a posterior cruciate ligament and the tibia, to an anterior point disposed on an anterior tubercle of the tibia, the tubercle having a width (W), the anterior point disposed on the tubercle at a location medially spaced from a midpoint of the tubercle by an amount equal to about W/6.

In Example 9, the family of tibial baseplates of any one or any combination of Examples 1-8 is optionally configured such that each of the plurality of tibial baseplates is configured to provide substantial coverage of a resected proximal tibia surface area and remain within a resected tibial periphery of the resected proximal tibia.

In Example 10, the family of tibial baseplates of any one or any combination of Examples 1-9 is optionally configured such that the tibial baseplate periphery of each of the plurality of tibial baseplates corresponds to at least one of an asymmetrical tibial periphery, a boxy tibial periphery, a minor asymmetrical tibial periphery, a rounded rectangular tibial periphery, and a rounded square tibial periphery.

In Example 11, the family of tibial baseplates of any one or any combination of Examples 1-10 is optionally configured such that each of the plurality of tibial baseplates comprises a chamfer on a medial side.

In Example 12, the family of tibial baseplates of any one or any combination of Examples 1-11 is optionally configured such that each of the plurality of tibial baseplate peripheries is configured to provide a gap between the tibial baseplate periphery and a periphery of a resected proximal tibia.

In Example 13, the family of tibial baseplates of any one or any combination of Examples 1-12 is optionally configured such that the gap varies in width, and wherein soft-tissue edges of the resected proximal tibia have an increased gap width.

In Example 14, a method of mounting a tibial baseplate on a resected proximal tibia comprises obtaining or providing a tibial baseplate from a family of common sized tibial baseplates each defining a unique, non-congruent tibial baseplate periphery as compared to the other tibial baseplates of the family of tibial baseplates, each tibial baseplate of the family including; an anteroposterior axis configured to divide the tibial baseplate periphery into a medial compartment and a lateral compartment; a lateral posterior edge generally opposite an anterior edge of the tibial baseplate periphery and forming a posterior boundary of the lateral compartment, the lateral compartment defining a lateral anteroposterior extent extending from the anterior edge of the tibial baseplate periphery to the lateral posterior edge thereof; and a medial posterior edge generally opposite the anterior edge of the tibial baseplate periphery and forming a posterior boundary of the medial compartment, the medial compartment defining a medial anteroposterior extent extending from the anterior edge of the tibial baseplate periphery to the medial posterior edge thereof. Wherein the medial anteroposterior extent being larger than the lateral anteroposterior extent; and aligning the tibial baseplate with a home axis of the resected proximal tibia, the home axis defined as a line segment extending from a posterior point at a geometric center of an attachment area between a posterior cruciate ligament and the tibia, to an anterior point disposed on an anterior tubercle of the tibia, the tubercle having a width (W), the anterior point disposed on the tubercle at a location medially spaced from a midpoint of the tubercle by an amount equal to about W/6.

In Example 15, the method of Example 14 is further configured such that obtaining or providing the tibial baseplate further comprises matching the baseplate periphery of each of the plurality of tibial baseplates with a tibial periphery of a resected proximal tibia, wherein the tibial periphery is at least one of an asymmetrical tibial periphery, a boxy tibial periphery, a minor asymmetrical tibial periphery, a rounded rectangular tibial periphery, and a rounded square tibial periphery.

In Example 16, the method of any one or any combination of Examples 14-15 is optionally configured such that the medial anteroposterior extent is the longest line segment within the medial compartment.

In Example 17, the method of any one or any combination of Examples 14-16 is optionally configured such that the lateral anteroposterior extent is the longest line segment within the lateral compartment.

In Example 18, the method of any one or any combination of Examples 14-17 is optionally configured such that aligning further comprises providing a gap between the tibial baseplate periphery and a tibial periphery of a resected proximal tibia.

In Example 19, the method of any one of any combination of Examples 14-18 is further configured such that each of the tibial baseplate peripheries is asymmetrical with respect to the anteroposterior axis.

In Example 20, a family of tibial baseplates comprises a plurality of tibial baseplates having a common size, each tibial baseplate defining a unique, non-congruent tibial baseplate periphery as compared to the other tibial baseplates of the family of tibial baseplates. Each tibial baseplate of the family includes an anteroposterior axis configured to divide the tibial baseplate periphery into a medial compartment and a lateral compartment, the anteroposterior axis configured to be aligned with a home axis when mounted to a resected proximal tibia, the home axis defined as a line segment extending from a posterior point at a geometric center of an attachment area between a posterior cruciate ligament (PCL) and the tibia, to an anterior point disposed on an anterior tubercle of the tibia, the tubercle having a width (W), the anterior point disposed on the tubercle at a location medially spaced from a midpoint of the tubercle by an amount equal to about W/6. Each tibial baseplate of the family includes a lateral posterior edge generally opposite an anterior edge of the tibial baseplate periphery and forming a posterior boundary of the lateral compartment, the lateral compartment defining a lateral anteroposterior extent extending from the anterior edge of the tibial baseplate periphery to the lateral posterior edge thereof, and a medial posterior edge generally opposite the anterior edge of the tibial baseplate periphery and forming a posterior boundary of the medial compartment, the medial compartment defining a medial anteroposterior extent extending from the anterior edge of the tibial baseplate periphery to the medial posterior edge thereof, wherein the medial anteroposterior extent is larger than the lateral anteroposterior extent. Each tibial baseplate of the plurality of tibial baseplates further includes a PCL cutout area generally opposite the anterior edge of the tibial baseplate periphery and between the medial compartment and the lateral compartment, wherein the PCL cutout is bisected by the anteroposterior axis.

In Example 21, the family of tibial baseplates or method of anyone one or any combination of Examples 1-20 is optionally configured such that all elements or options recited are available to use or select from.

These and other examples and features of the present tibial baseplates and methods will be set forth in part in the following Detailed Description. This Summary is intended to provide non-limiting examples of the present subject matter—it is not intended to provide an exclusive or exhaustive explanation. The Detailed Description below is included to provide further information about the present tibial baseplates and methods.

It has been found that substantial tibial coverage can be achieved for a large portion of patients using tibial baseplates having asymmetric peripheries in accordance with the present disclosure. Further, the particular asymmetry of a tibial baseplate in accordance with the present disclosure can be expected to offer such coverage without overhanging any portion of a resected tibia surface.

Thus, asymmetric tibial peripheries as described herein can confer one or more benefits including, for example, maximum coverage, facilitation of proper rotation, and long-term fixation. Such asymmetry can be demonstrated in various ways, including: a medial anteroposterior extent; a lateral anteroposterior extent; a mediolateral extent; a medial compartment surface area; or a lateral compartment surface area.

Advantageously, the asymmetry of the tibial baseplate examples described herein can encourage proper rotational orientation of the baseplate upon implantation thereof onto a tibia. As described herein, the asymmetry of the tibial baseplate periphery can be designed to provide a close match in selected areas of the lateral and medial compartments as compared to the anatomic bone. As such, a surgeon can select the largest or best fitting tibial baseplate, such that the component substantially covers the resected tibia with minimal gaps between the tibial periphery and the baseplate periphery, with little to no overhang of any portions of the baseplate periphery. Because of the minimal gap between the tibia and baseplate peripheries, the tibial baseplate cannot be rotated significantly without causing the tibial baseplate to overhang beyond the periphery of the resected tibial surface. Thus proper rotation of the baseplate can be ascertained by the visual acuity between the baseplate periphery and the resected tibial surface.

To achieve greater tibial coverage, a tibial baseplate can be selected that closely matches the periphery of the resected tibia in most areas, as noted above. However, a small gap between the baseplate periphery and the tibia can be formed to allow some freedom of positioning or rotational orientation. The gap can be designed to have a substantially continuous width in most areas, including the anterior edge, anterior-medial corner, medial edge, lateral edge, or lateral-posterior corner. However, certain examples contemplate deviating from a continuous gap width, such as a greater gap width for soft-tissue edges. For example, an anterior-lateral corner can have an increased gap width to accommodate the iliotibial band, so as to minimize impingement.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

DETAILED DESCRIPTION

The present disclosure describes a set of tibial baseplates in which each baseplate defines a unique outer asymmetrical periphery adapted to cooperate with a particular subset of anatomic tibial geometries. Each unique baseplate periphery can be adapted to provide substantial coverage of a resected proximal surface of a tibia within one or more population subsets.

As used herein and unless stated otherwise, proximal refers to a direction generally toward the torso of a patient, and distal refers to the opposite direction of proximal, such as away from the torso of the patient.

As used herein and unless stated otherwise, a periphery of a tibial baseplate refers to any periphery as viewed in a top plan view or a bottom plan view, such as in a generally transverse anatomical plane.

As used herein and unless stated otherwise, an anterior direction is a direction toward the front a patient along the home axis $A_H$ (FIGS. 1B, 1C, 2B, 3B, 4B, and 5B). A posterior direction is the opposite of anterior, such as toward the back of a patient along the home axis $A_H$. Medial and lateral directions run generally perpendicular to home axis $A_H$, and toward the inside and outside of the knee, respectively.

Figure 1:
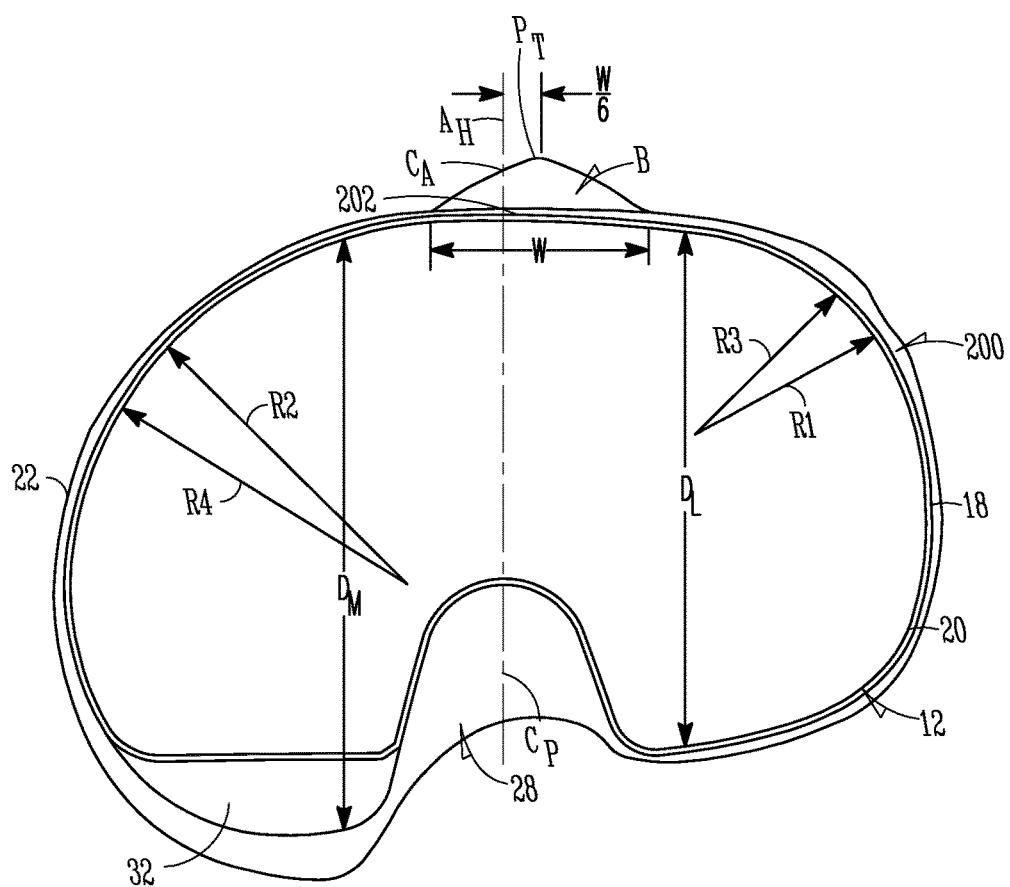
FIG. 1 is a top plan view of an exemplary tibial baseplate, shown implanted upon a resected tibia, in accordance with at least one example.

Referring to FIG. 1, by way of example, a tibia T can include a tibial tubercle B having a mediolateral width W, with a tubercle midpoint $P_T$ located on the tubercle B approximately halfway across the width W. While the tubercle B is shown as having the midpoint $P_T$ at the peak or point of maximum anterior eminence, it is recognized that the midpoint $P_T$ of the tibia T can be spaced from such a peak. The tibia T can also include an attachment point $C_P$ representing the geometric center of the attachment area between the anatomic posterior cruciate ligament (PCL) and the tibia T. Recognizing that the PCL typically attaches to a tibia in two ligament bundles, one of which is relatively anterior, lateral, and proximal, and the other of which is relatively posterior, medial, and distal, the attachment point $C_P$ is contemplated as representing the anterior-lateral attachment area in an exemplary embodiment. However, it is contemplated that the posterior-medial attachment area, or the entire attachment area, could be used.

In the context of patient anatomy, the home axis $A_H$ refers to a generally anteroposterior axis of a tibia extending from the posterior point $C_P$ to an anterior point $C_A$. The anterior point $C_A$ can be disposed on the tubercle B and medially spaced from the tubercle midpoint $P_T$ by an amount equal to about W/6, wherein a mediolateral width is represented by the mediolateral width W. Stated another way, the anterior point $C_A$ can be laterally spaced by an amount about equal to about W/3 from the medial end of the mediolateral width W, such that the point $C_A$ lies on the "medial third" of the anterior tibial tubercle. The posterior point $C_P$ is the attachment point between the anatomic PCL and the tibia.

In the context of a prosthesis, such as a first tibial baseplate 12 shown in FIG. 1, the home axis $A_H$ can refer to an axis oriented with respect to the baseplate 12 such that an anteroposterior axis of the baseplate 12 is substantially aligned with the home axis $A_H$ of the tibia T after implantation of the baseplate 12 in a desired rotational and spatial orientation. In the illustrative examples shown and described in detail below, the home axis $A_H$ can bisect a PCL cutout 28 at the posterior edge of a periphery 200 of a tibial plateau 18, and can bisect an anterior edge 202 at the periphery 200 of the tibial plateau 18. It is contemplated that the home axis $A_H$ can be oriented to other baseplate features; it being understood that the anteroposterior axis of the first tibial baseplate 12 is positioned such that that desired alignment and orientation of the baseplate 12 upon the tibia T positions the anteroposterior axis of the baseplate 12 coincident with the home axis $A_H$ of tibia T.

The examples shown and described herein illustrate a right knee and associated features of a right-knee prosthesis, with the exception of FIG. 1 which illustrates a left knee prosthesis. Right and left knee configurations are mirror images of one another about a sagittal plane. Thus, it will be appreciated that all aspects of the prosthesis described herein are equally applicable to a left or right knee configuration. Further, the tibial baseplates described herein can be of the same common, nominal size. That is, each tibial baseplate can be sized to fit the same size patient. However, each baseplate described herein can be unique or non-congruent as compared to other tibial baseplates described herein. For example, a tibial periphery of each baseplate can be unique compared to other tibial baseplates as described herein.

Figure 2A:
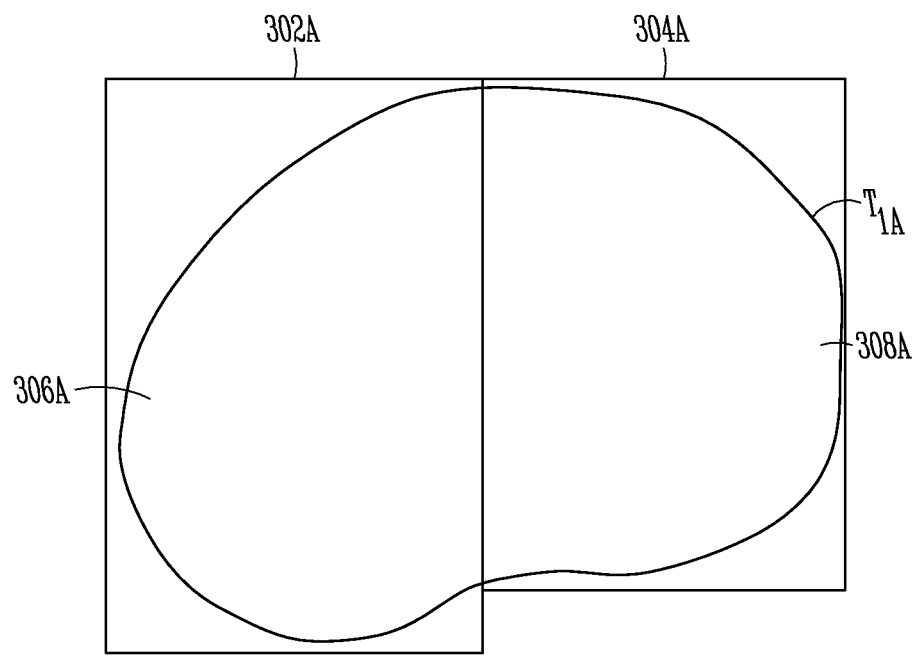
FIG. 2A illustrates a tibial periphery appropriate for use with a tibial baseplate, in accordance with at least one example.
Figure 2B:
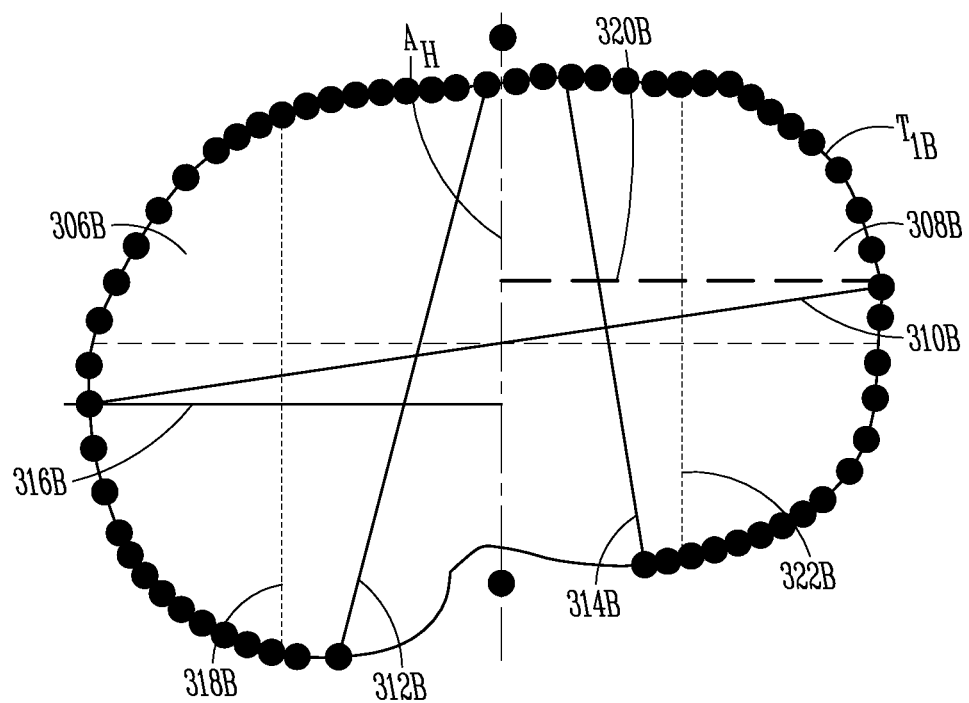
FIG. 2B illustrates the tibial periphery of FIG. 2A appropriate for use with a tibial baseplate, in accordance with at least one example.

Turning to FIGS. 2A and 2B, schematic representations of anatomic tibial peripheries $T_{1A}$, $T_{1B}$ are illustrated. Reference numerals of FIG. 2A generally correspond with the reference numerals of FIG. 2B, with the numerals of FIG. 2B having a "B" appended thereto except as otherwise noted. FIGS. 2A and 2B show a special patient population with an asymmetrical tibial periphery.

A periphery $T_{1A}$ (FIG. 2A) is shown in the context of a pair of adjacent, circumscribing rectangles 302A, 304A, in which a medial rectangle 302A bounds a medial compartment 306A of the periphery $T_{1A}$, while a lateral rectangle 304A bounds a lateral compartment 308A thereof. A Periphery $T_{1B}$ (FIG. 2B) illustrates a maximum width 310B, which is the longest line segment that can be drawn within the confines of the periphery $T_{1B}$. The periphery $T_{1A}$ can represent the actual periphery of the tibia, whereas $T_{1B}$ can represent a modeled periphery of the tibia. Similarly, a medial length 312B is the longest line segment that can be drawn within the confines of the medial compartment 306B, and a lateral length 314B is the longest line segment that can be drawn within the confines of the lateral compartment 308B. In the context of the coordinate system of a tibial prosthesis (e.g., the first tibial baseplate 12 discussed herein), the medial compartment 306B defines a compartment medial-lateral extent 316B and a compartment anteroposterior extent 318B, while the lateral compartment 308B defines a compartment medial-lateral extent 320B and a compartment anteroposterior extent 322B.

With reference again to FIG. 1, the first tibial baseplate 12 can be configured in accordance with the present disclosure to substantially cover the area bounded by tibial periphery $T_{1A}$, while also remaining substantially or completely within this area. The first tibial baseplate 12 can have a general asymmetry in which a medial compartment 22, such as the baseplate compartment sized to correspond with the medial compartments 306A, 306B of peripheries $T_{1A}$, $T_{1B}$, has a disparate peripheral geometry with respect to a lateral compartment 20, such as the baseplate compartment sized to correspond with the lateral compartments 308A, 308B of peripheries $T_{1A}$, $T_{1B}$.

For example, the medial compartment 22 of the first tibial baseplate 12 can define an overall anteroposterior extent $D_M$, corresponding to, but shorter than, the anteroposterior extent 318B of the periphery $T_{1B}$, as shown in FIG. 2B. The anteroposterior extent $D_M$ can be larger than a corresponding anteroposterior extent $D_L$ of the lateral compartment 20, corresponding to, but shorter than, the anteroposterior extent 322B of the periphery $T_{1B}$, as shown in FIG. 2B. In some examples, the first tibial baseplate 12 can include an overall mediolateral extent corresponding to, but shorter than the maximum width 310B. As used herein, an overall extent or extent refers to the longest line segment within a given compartment or periphery. For example, the anteroposterior extent $D_M$ can be the longest anteroposterior line segment within the medial compartment. Further, the anteroposterior extent $D_L$ can be the longest anteroposterior line segment within the lateral compartment. The mediolateral extent can be the longest anteroposterior line segment within the tibial baseplate periphery, such as the greatest width of the first tibial baseplate 12.

As illustrated in FIG. 1, the overall anteroposterior extent $D_M$ can include a chamfer 32 of the first tibial baseplate 12, as described in U.S. Patent Application Publication Nos. 2012/0022659, 2012/0022660, and 2012/0022658, each filed Jul. 22, 2011 and entitled "Asymmetric Tibial Components for a Knee Prosthesis", the entire disclosures of which are hereby expressly incorporated herein by reference.

The medial compartment 22 can also define an anterior-medial corner of the baseplate periphery 200 having a broadly rounded, large-radius curvature including radii $R_2$ and $R_4$, which are sized to correspond with the anterior-medial corner of the periphery $T_{1A}$, such as the portion of the periphery at the upper left of the portion of periphery $T_{1A}$ bounded by the medial rectangle 302A. Other corners of the baseplate periphery 200, such as anterior-lateral, posterior-medial, or posterior-lateral can define smaller radii and, therefore, make "tighter" turns. For example, radii $R_1$ and $R_3$ can define the anterior-lateral corner of the periphery 200, and can be substantially smaller than radii $R_2$ and $R_4$.

Figure 3A:
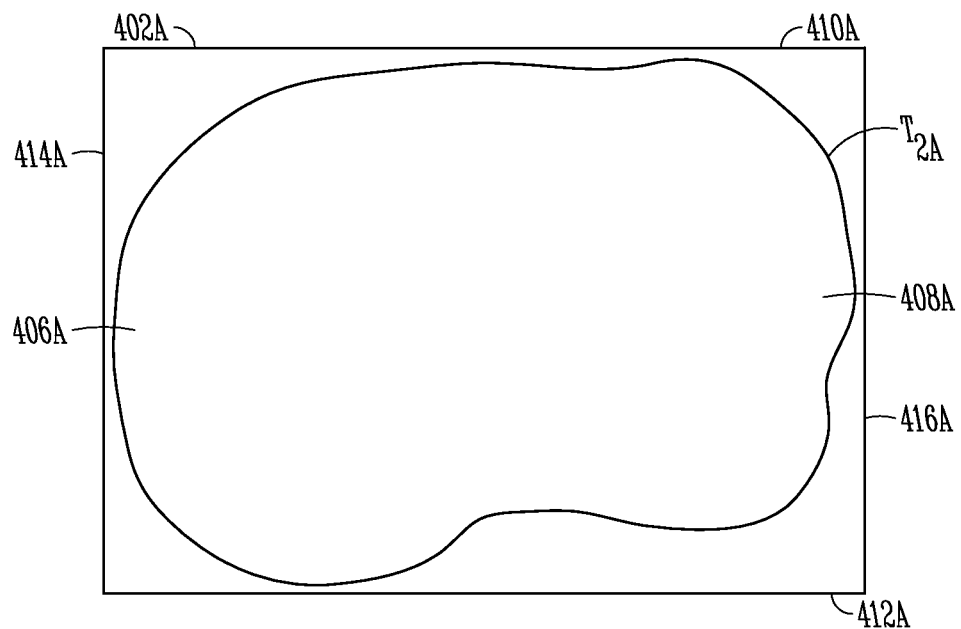
FIG. 3A illustrates a tibial periphery appropriate for use with a tibial baseplate, in accordance with at least one example.
Figure 3B:
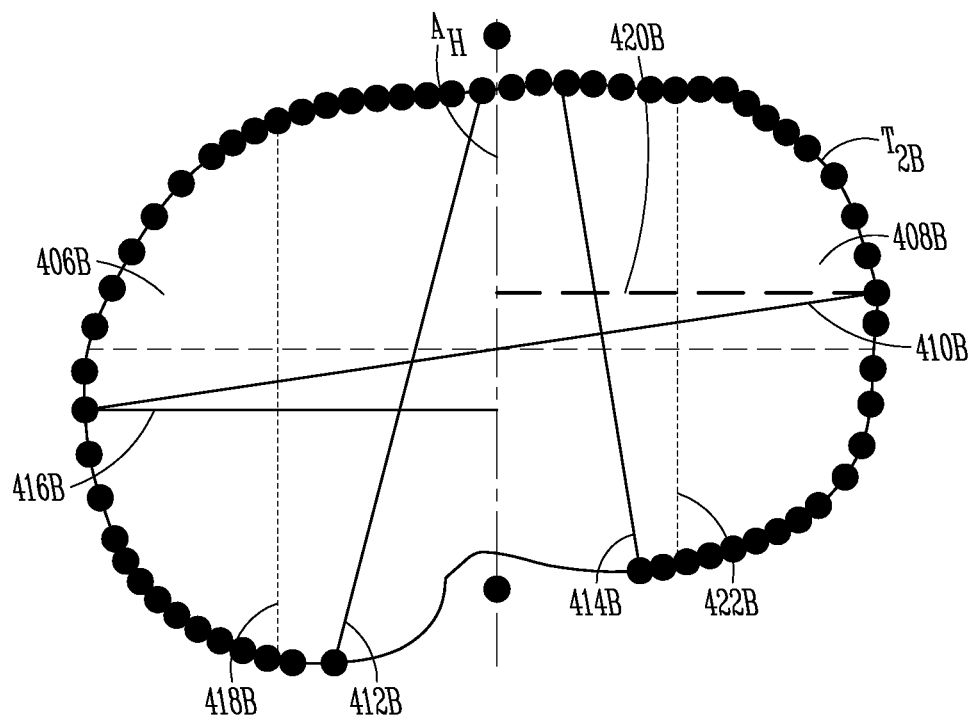
FIG. 3B illustrates the tibial periphery of FIG. 3A appropriate for use with a tibial baseplate, in accordance with at least one example.

Turning to FIGS. 3A and 3B, schematic representations of anatomic tibial peripheries $T_{2A}$, $T_{2B}$ having a relatively "boxy" profile, as compared to the tibial peripheries $T_{1A}$, $T_{1B}$, are illustrated. Reference numerals of FIG. 3A generally correspond with the reference numerals of FIG. 3B, with the numerals of FIG. 3B having a "B" appended thereto except as otherwise noted. FIGS. 3A and 3B represent a special patient population with a "boxy" tibial periphery.

The "boxy" tibial periphery $T_{2A}$ of FIG. 3A is circumscribed by a rectangle 402A. The rectangle 402A includes anterior and posterior sides 410A, 412A tangent to the anterior-most and posterior-most portions of the periphery $T_{2A}$, respectively. The anterior and posterior sides 410A, 412A extend along generally medial-lateral directions. Medial and lateral sides 414A, 416A bound the medial and lateral portions of the periphery $T_{2A}$, such that the medial side 414A is substantially tangent to the medial compartment 406A and the lateral side 416A is substantially tangent to the lateral compartment 408A. The medial and lateral sides 414A, 416A extend along a generally anteroposterior direction.

The periphery $T_{2B}$ of FIG. 3B includes a maximum width 410B, which is the longest line segment that can be drawn within the confines of the periphery $T_{2B}$. As also shown in FIG. 3B, the periphery $T_{2B}$ can include a medial length 412B, which is the longest line segment that can be drawn within the confines of the medial compartment 406B, and a lateral length 414B, which is the longest line segment that can be drawn within the confines of lateral compartment 408B. In the context of the coordinate system of a tibial prosthesis, such as the second tibial baseplate discussed below, the medial compartment 406B can define a medial-lateral extent 416B and an anteroposterior extent 418B, while the lateral compartment 408B can define a medial-lateral extent 420B and an anteroposterior extent 422B.

A second tibial baseplate can be provided which is designed to substantially cover the area bounded by the peripheries $T_{2A}$, $T_{2B}$ without crossing peripheries $T_{2A}$, $T_{2B}$ at any point; that is, without overhanging a resected tibia having a periphery similar to peripheries $T_{2A}$, $T_{2B}$. The second tibial baseplate can differ from first tibial baseplate 12 in that the medial compartment, e.g., the compartment of the second tibial baseplate sized to correspond with the medial compartments 406A, 406B of the periphery $T_{2A}$, $T_{2B}$, of the second tibial baseplate can define a smaller radius at the anterior-medial corner thereof, to accommodate the more "boxy" tibial peripheries $T_{2A}$, $T_{2B}$ as compared to the more "rounded" tibial periphery $T_{1A}$, $T_{1B}$ for example. In an example, the radius and peripheral geometry of the anterior-medial corner can be similar to the radius and peripheral geometry of the anterior-lateral corner.

Further, in an example of the second tibial baseplate, the disparity between the medial and lateral anteroposterior extents can be comparable to the first tibial baseplate 12, with the second tibial baseplate being asymmetric in similar fashion to first tibial baseplate 12. However, it is contemplated that the asymmetry of the second tibial baseplate periphery can be more or less pronounced. For example, the second tibial baseplate can define a medial compartment having an anteroposterior extent which is relatively less or more disparate from the anteroposterior extent defined by the lateral baseplate compartment, as compared to the relatively greater corresponding disparity defined by the first tibial baseplate 12.

Figure 4A:
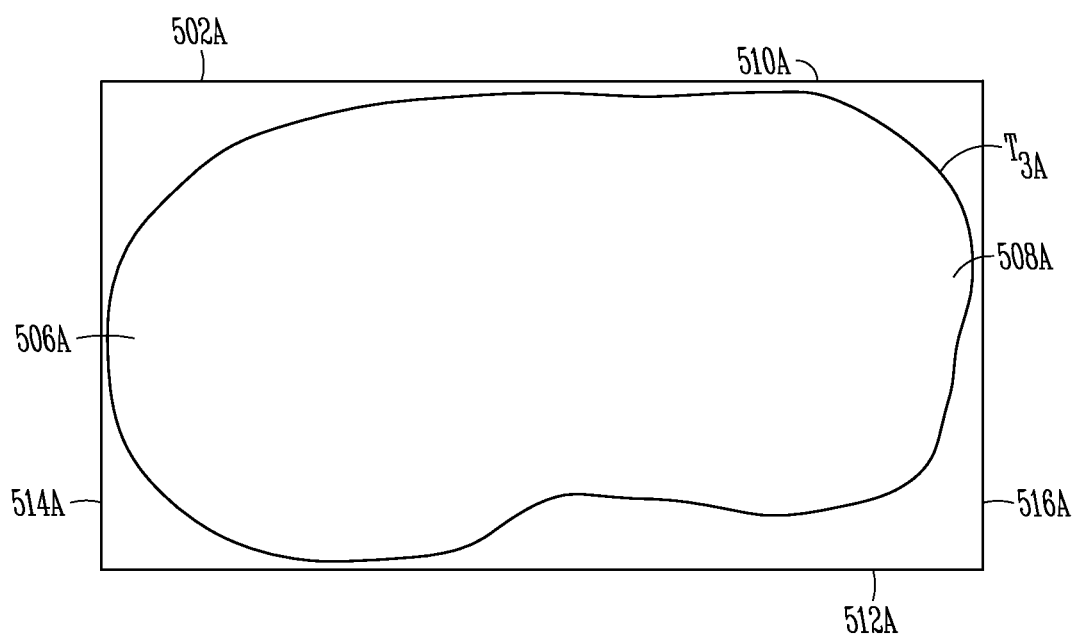
FIG. 4A illustrates a tibial periphery appropriate for use with a tibial baseplate, in accordance with at least one example.
Figure 4B:
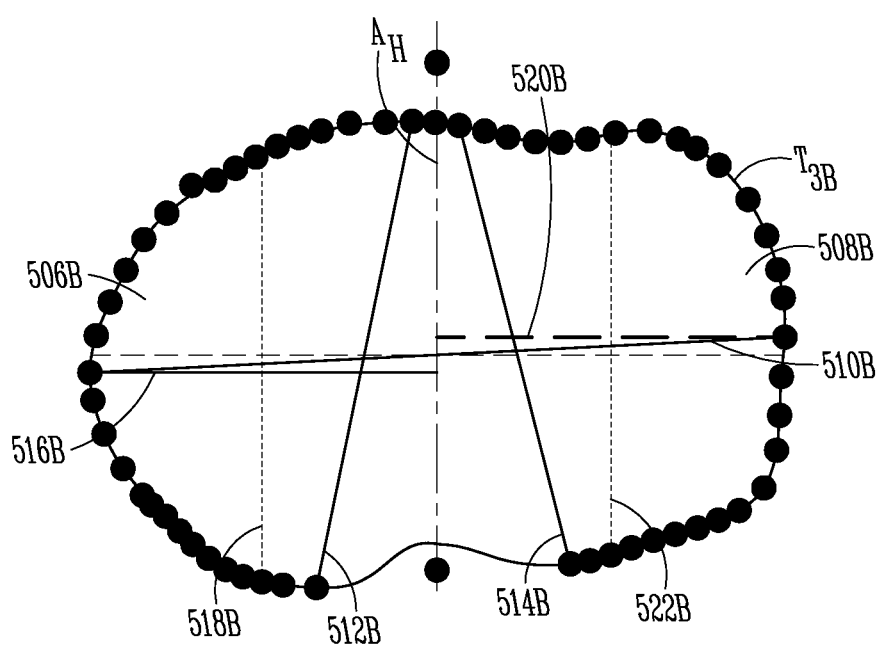
FIG. 4B illustrates the tibial periphery of FIG. 4A appropriate for use with a tibial baseplate, in accordance with at least one example.

Turning to FIGS. 4A and 4B, schematic representations of anatomic tibial peripheries $T_{3A}$, $T_{3B}$ having a minor asymmetric profile (as described in detail below) are illustrated. Reference numerals of FIG. 4A generally correspond with the reference numerals of FIG. 4B, with the numerals of FIG. 4B having a "B" appended thereto except as otherwise noted. FIGS. 4A and 4B show a special patient population with a minor asymmetric or less-asymmetric tibial periphery, as compared to the tibial periphery $T_{1A}$, for example. As illustrated in FIG. 4A, the less-asymmetric tibial periphery $T_{3A}$ is bounded by a rectangle 502A. The rectangle 502A defines sides 510A, 512A, 514A, 516A which are analogous to sides 410A, 412A, 414A, 416A described above with respect to FIG. 3A.

The periphery $T_{3B}$ of FIG. 4B illustrates a maximum width 510B, which is the longest line segment that can be drawn within the confines of the periphery $T_{3B}$. As also shown in FIG. 4B, the periphery $T_{3B}$ can include a medial length 512B, which is the longest line segment that can be drawn within the confines of a medial compartment 506B, and lateral length 514B, which is the longest line segment that can be drawn within the confines of a lateral compartment 508B. In the context of the coordinate system of a tibial prosthesis, such as the third tibial baseplate discussed below, the medial compartment 506B can define a medial-lateral extent 516B and an anteroposterior extent 518B, while the lateral compartment 508B can defines a medial-lateral extent 520B and an anteroposterior extent 522B. The peripheries $T_{3A}$, $T_{3B}$ are generally similar to the peripheries $T_{1A}$, $T_{1B}$ discussed above, except that the disparity between the medial and lateral lengths 512B, 514B is less than the corresponding disparity between the corresponding lengths 312B, 314B of periphery $T_{1B}$. Thus, it can be said that peripheries $T_{3A}$, $T_{3B}$ define a minor asymmetry as compared to the peripheries $T_{1A}$, $T_{1B}$.

A third tibial baseplate in accordance with the present disclosure can be configured to provide substantial coverage of the area defined by the tibial peripheries $T_{3A}$, $T_{3B}$, without crossing the peripheries $T_{3A}$, $T_{3B}$ at any point, such as without overhanging a resected tibia having a periphery similar to the peripheries $T_{3A}$, $T_{3B}$. The third tibial baseplate can differ from the first and second tibial baseplates in that the third tibial baseplate defines an outer profile which is less asymmetric. For example, the geometric disparity between the medial and lateral baseplate compartments of the third tibial baseplate can be less than the geometric disparity present in the more asymmetric first tibial baseplate 12.

For example, the medial compartment of the third tibial baseplate (e.g., the compartment sized to correspond with the medial compartments 506A, 506B of the periphery $T_{3B}$) can define a medial anteroposterior extent which is only slightly larger than the corresponding lateral anteroposterior extent of the lateral compartment (e.g., the compartment sized to correspond with the medial compartments 508A, 508B of periphery $T_{3B}$). By comparison, the medial compartments of the first and second tibial baseplates define overall anteroposterior extents which are substantially larger than the anteroposterior extent of the respective adjacent lateral compartments, thereby defining a relatively greater disparity as compared to the third tibial baseplate.

Figure 5A:
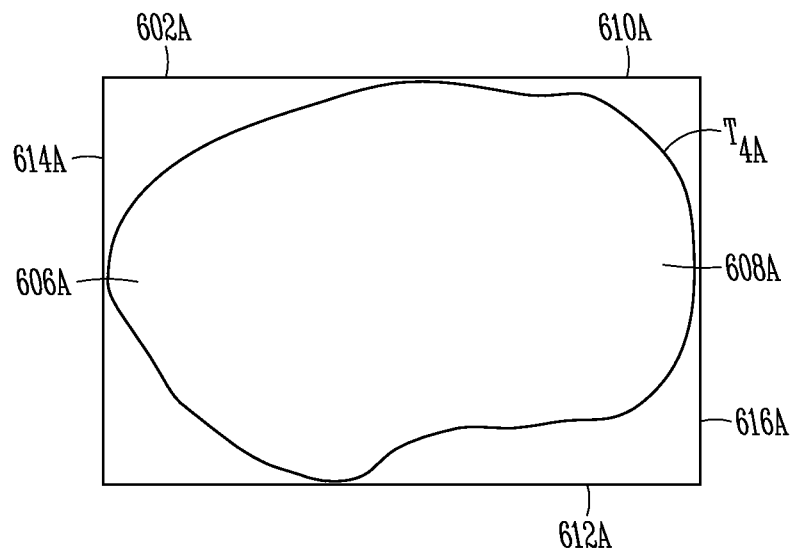
FIG. 5A illustrates a tibial periphery appropriate for use with a tibial baseplate, in accordance with at least one example.
Figure 5B:
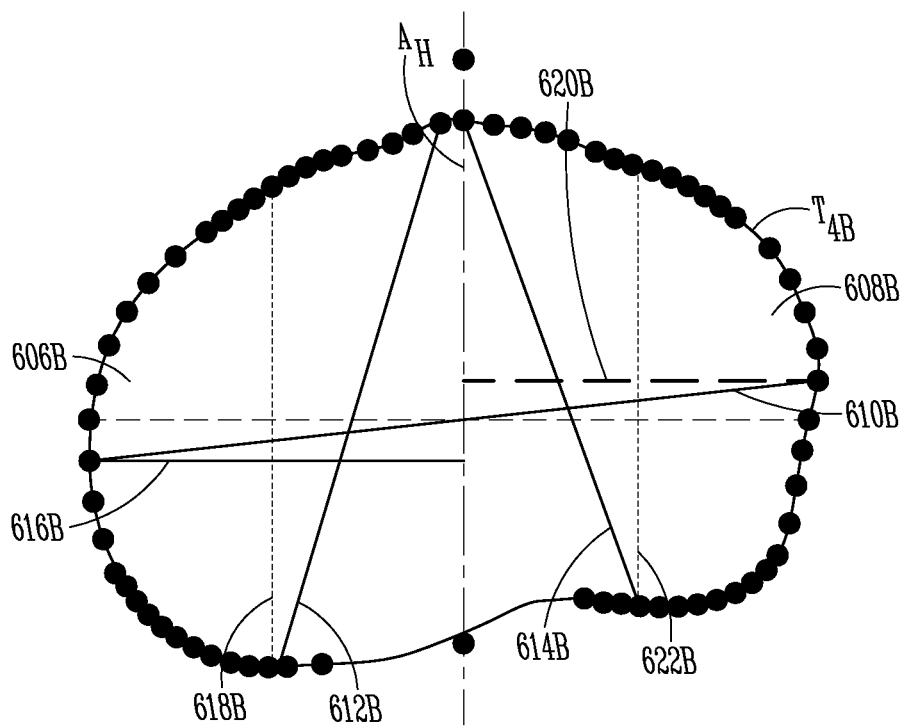
FIG. 5B illustrates the tibial periphery of FIG. 5A appropriate for use with a tibial baseplate, in accordance with at least one example.

Turning to FIGS. 5A and 5B, schematic representations of anatomic tibial peripheries $T_{4A}$, $T_{4B}$ having a rounded, rectangular asymmetric profile, as compared to the peripheries $T_{1A}$, $T_{1B}$, are illustrated. Reference numerals of FIG. 5A generally correspond with the reference numerals of FIG. 5B, with the numerals of FIG. 5B having a "B" appended thereto except as otherwise noted. FIGS. 5A and 5B show a special patient population with a rounded, rectangular tibial periphery. As illustrated in FIG. 5A, an asymmetric tibial periphery $T_{4A}$ is bounded by a rectangular bounding box 602A similar to bounding box 402A of the tibial periphery $T_{2A}$. However, anterior and posterior sides 610A, 612A are substantially longer than medial and lateral sides 614A, 616A, such that a rectangle 602A is more elongate than the rectangle 402A defined by periphery $T_{2A}$.

The periphery $T_{4B}$ of FIG. 5B illustrates a maximum width 610B, which is the longest line segment that can be drawn within the confines of periphery $T_{4B}$. As also shown in FIG. 5B, the periphery $T_{4B}$ can include a medial length 612B, which is the longest line segment that can be drawn within the confines of a medial compartment 606B, and lateral length 614B, which is the longest line segment that can be drawn within the confines of a lateral compartment 608B. In the context of the coordinate system of a tibial prosthesis, such as the fourth tibial baseplate discussed below, the medial compartment 606B can define a medial-lateral extent 616B and an anteroposterior extent 618B, while the lateral compartment 608B can define a medial-lateral extent 620B and an anteroposterior extent 622B. The rounded, asymmetric profile of the tibial periphery $T_{4B}$ can mean that medial and lateral anteroposterior extents 618B, 622B each represent a relatively smaller percentage of a medial-lateral width 610B of the periphery $T_{4A}$, as compared to the corresponding percentages defined by the periphery $T_{2A}$.

Tibial peripheries $T_{4A}$, $T_{4B}$ are asymmetric, in that the medial and lateral anteroposterior extents 618B, 622B are disparate from one another in similar fashion to peripheries $T_{1A}$, $T_{1B}$. However, the general asymmetry of the tibial peripheries $T_{1A}$, $T_{1B}$, can be defined by a broadly rounded, large radius anterior-medial corner joined to a "boxy" posterior-medial corner by a relatively flat anterior edge, as shown in FIGS. 2A and 2B and described above. By contrast, the peripheries $T_{4A}$, $T_{4B}$ can be broadly rounded across the anterior edge, such that radii at both the anterior-medial and anterior-lateral portions are joined by another broadly radiused portion.

A fourth tibial baseplate can be provided with a periphery configured to provide substantial coverage of the tibial peripheries $T_{4A}$, $T_{4B}$, without crossing the peripheries $T_{4A}$, $T_{4B}$ at any point, such as without overhanging the peripheries $T_{4A}$, $T_{4B}$. The fourth tibial baseplate can have medial and lateral compartments corresponding with medial compartments 606A, 606B, and lateral compartments 608A, 608B of the tibial peripheries $T_{4A}$, $T_{4B}$ when implanted. More specifically, the fourth tibial baseplate can have a rounded anterior edge disposed between the anterior-lateral and anterior-medial corners of the baseplate periphery.

Further, the fourth tibial baseplate can be relatively more elongate along the medial-lateral direction as compared to first tibial baseplate 12. That is to say, the fourth tibial baseplate can include medial and lateral compartments (e.g., the compartments sized to correspond with the medial compartments 606A, 606B and the lateral compartments 608A, 608B of the periphery $T_{4B}$, respectively) whose overall anteroposterior extents represent a smaller percentage of the overall medial-lateral extent of the fourth tibial baseplate as compared to first tibial baseplate 12.

Figure 6A:
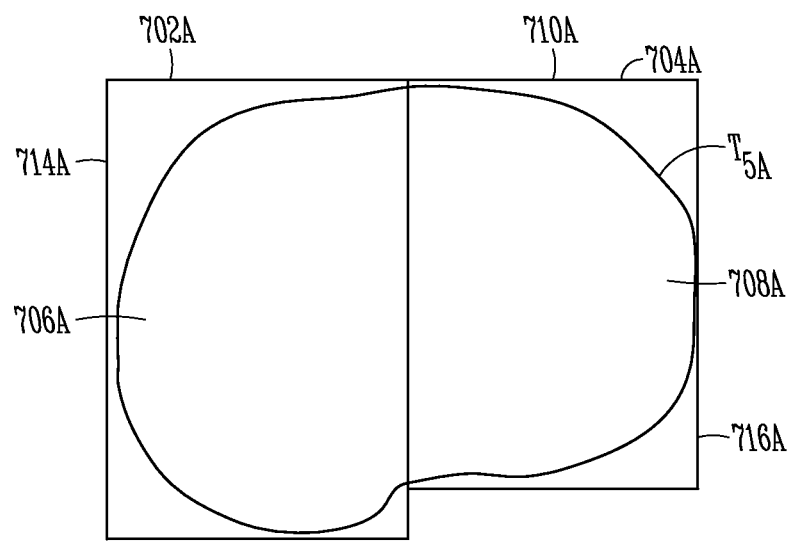
FIG. 6A illustrates a tibial periphery appropriate for use with a tibial baseplate, in accordance with at least one example.
Figure 6B:
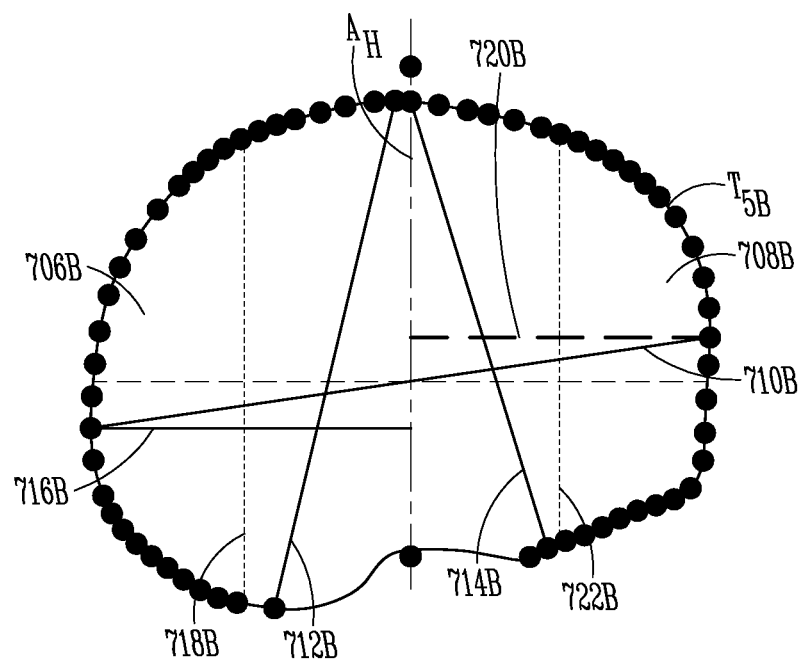
FIG. 6B illustrates the tibial periphery of FIG. 6A appropriate for use with a tibial baseplate, in accordance with at least one example.
Figure 7A:
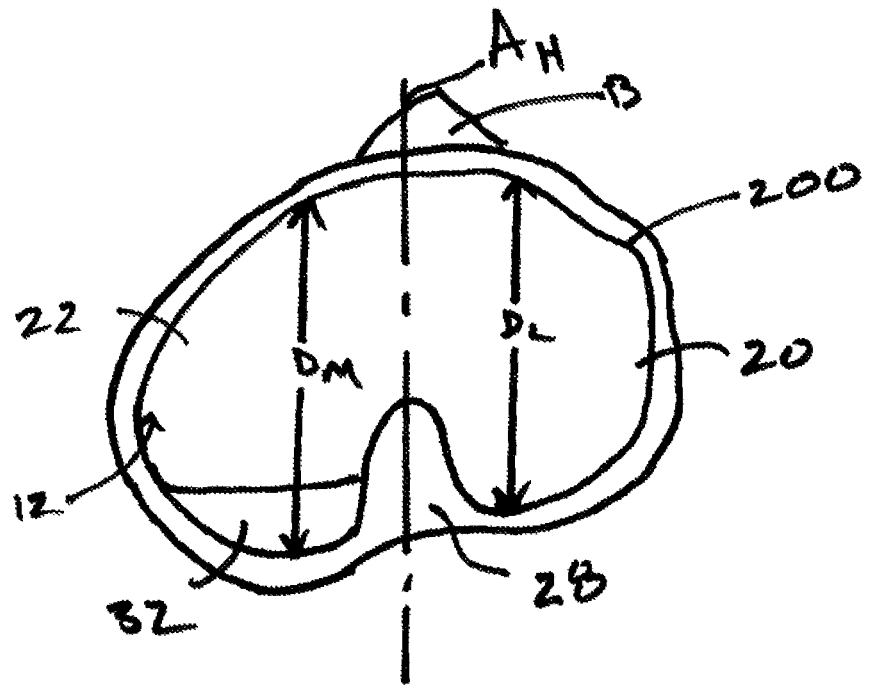
FIGS. 7A-E illustrate exemplary tibial baseplates appropriate for use with the tibial peripheries illustrated in FIGS. 2A-6B, shown implanted upon a resected tibia, in accordance with at least one example
Figure 7B:
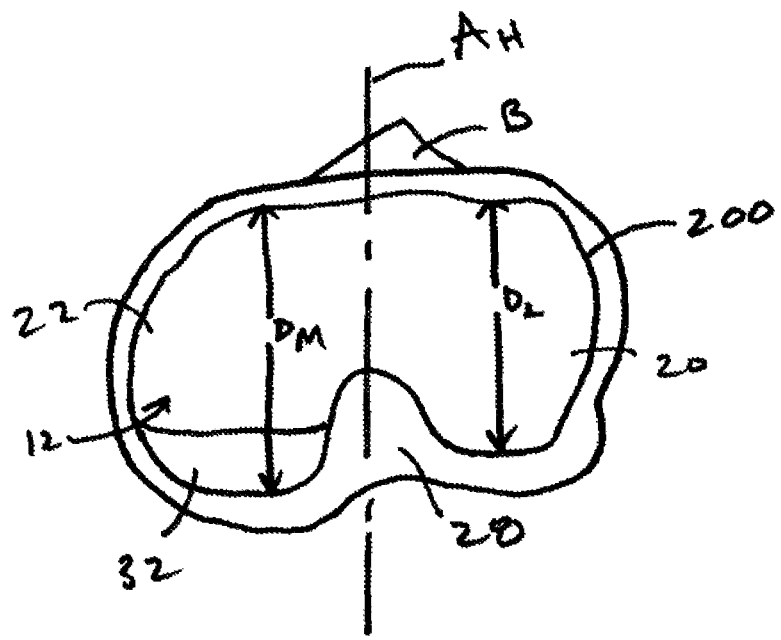
Figure 7C:
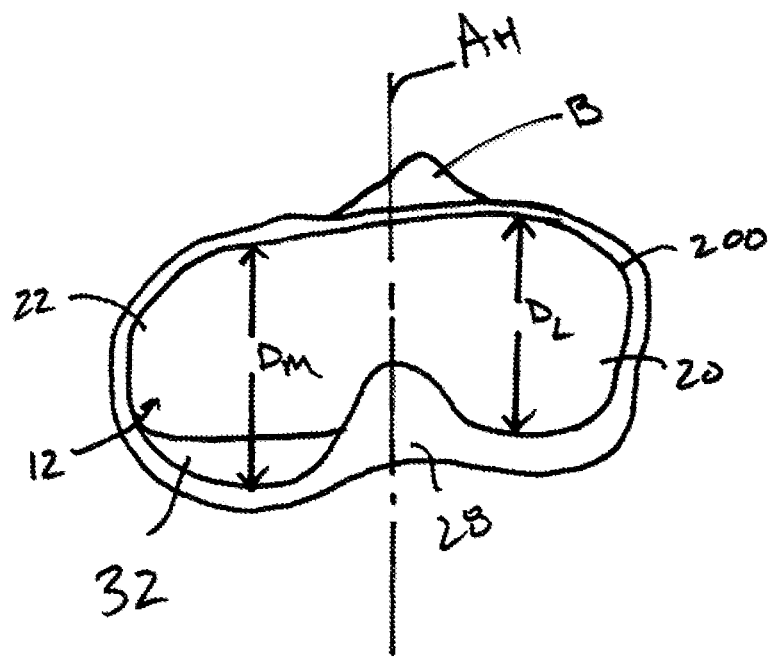
Figure 7D:
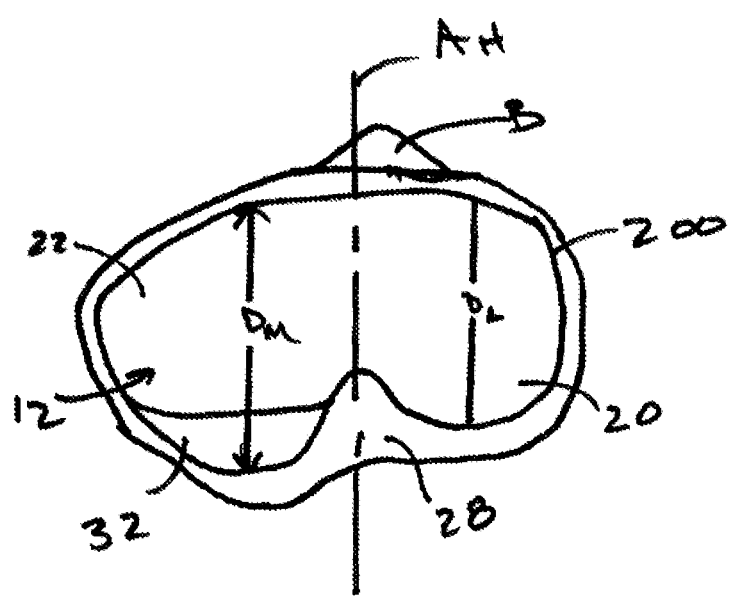
Figure 7E:
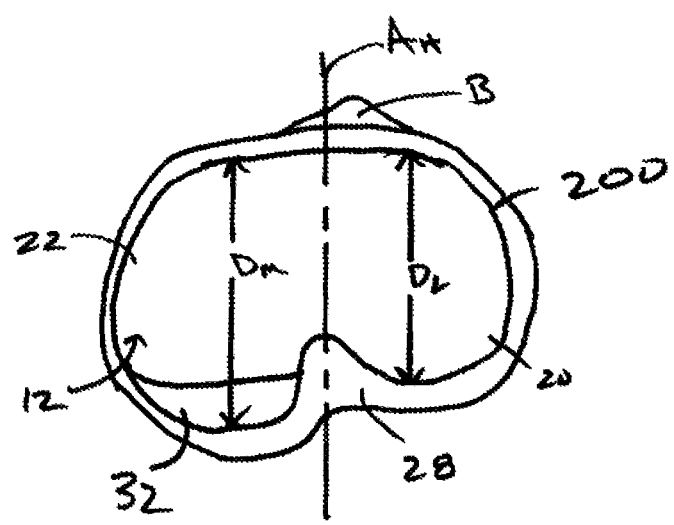

Turning now to FIGS. 6A and 6B, schematic representations of anatomic tibial peripheries $T_{5A}$, $T_{5B}$ having a rounded, square-like asymmetric profile, as compared to the peripheries $T_{1A}$, $T_{1B}$, are illustrated. Reference numerals of FIG. 6A generally correspond with the reference numerals of FIG. 6B, with the numerals of FIG. 6B having a "B" appended thereto except as otherwise noted. FIGS. 6A and 6B show a special patient population with a rounded, square tibial periphery.

As illustrated in FIG. 6A, tibial periphery $T_{5A}$ is bounded by medial and lateral rectangles 702A, 704A, which are adjacent to one another in similar fashion to rectangles 302A, 304A described above with respect to FIG. 2A. Compared to the relatively more elongate rectangular bounding box 612A, described above with respect to FIG. 5A, the rectangles 702A, 704A collectively define a more square-like bounding box around periphery $T_{5A}$. That is to say, a medial side 714A defines a larger percentage of an anterior side 710A, which spans the medial and lateral rectangles 702A, 704A, as compared to the medial and anterior sides 614A, 610A of periphery $T_{4A}$, such that the rectangle 702A is less elongate than the rectangle 602A defined by periphery $T_{4A}$.

The periphery $T_{5B}$ of FIG. 6B illustrates a maximum width 710B, which is the longest line segment that can be drawn within the confines of periphery $T_{5B}$. As also shown in FIG. 6B, the periphery $T_{5B}$ can include a medial length 712B, which is the longest line segment that can be drawn within the confines of a medial compartment 706B, and lateral length 714B, which is the longest line segment that can be drawn within the confines of a lateral compartment 708B. In the context of the coordinate system of a tibial prosthesis, such as the fifth tibial baseplate discussed below, the medial compartment 706B can define a medial-lateral extent 716B and an anteroposterior extent 718B, while lateral compartment 708B can define a medial-lateral extent 720B and an anteroposterior extent 722B. The rounded, asymmetric profile of the tibial periphery $T_{5B}$ can mean that medial and lateral anteroposterior extents 718B, 722B can each represent a larger percentage of a medial-lateral width 710B of periphery the $T_{5A}$, as compared to the corresponding percentages defined by the periphery $T_{4A}$ described above.

Tibial peripheries $T_{5A}$, $T_{5B}$ are asymmetric, in that the medial and lateral anteroposterior extents 718B, 722B are disparate from one another in similar fashion to peripheries $T_{1A}$, $T_{1B}$. However, similar to the rounded, asymmetric peripheries $T_{4A}$, $T_{4B}$, tibial peripheries $T_{5A}$, $T_{5B}$, can be generally broadly rounded across the anterior edge, such that radii at both the anterior-medial and anterior-lateral portions can be joined by another broadly radiused portion.

A fifth tibial baseplate can provide substantial coverage of the area bounded by the peripheries $T_{5A}$, $T_{5B}$, without crossing the peripheries $T_{5A}$, $T_{5B}$ at any point, such as without overhanging the peripheries $T_{5A}$, $T_{5B}$. The fifth tibial baseplate can have medial and lateral compartments corresponding with the medial compartments 706A, 706B, and the lateral compartments 708A, 708B of the tibial peripheries $T_{5A}$, $T_{5B}$ when implanted. More specifically, the fifth baseplate can have a rounded anterior edge disposed between the anterior-lateral and anterior-medial corners of the baseplate periphery.

The fifth tibial baseplate can be similar to first tibial baseplate 12 with regard to the anteroposterior extents of the medial and lateral baseplate compartments. That is to say, the fourth tibial baseplate can include medial and lateral compartments, such as the compartments sized to correspond with the medial compartments 706A, 706B and the lateral compartments 708A, 708B of peripheries $T_{5A}$, $T_{5B}$, respectively, whose overall anteroposterior extents are substantially disparate from one another, in similar fashion to the first tibial baseplate 12 described above.

It is contemplated that the differences between the second through fifth tibial baseplates as compared to first tibial baseplate 12 can be quantified in a variety of ways. For example, various exemplary measures of asymmetry and peripheral geometry are discussed in U.S. Patent Application Publication Nos. 2012/0022659, 2012/0022660, and 2012/0022658, incorporated by reference above, with reference to the first tibial baseplate 12. More particularly, the measures of asymmetry and peripheral geometry utilized to compare and quantify the medial and lateral compartments 22, 20 of the first tibial baseplate 12 in U.S. Patent Application Publication Nos. 2012/0022659, 2012/0022660, and 2012/0022658, incorporated by reference above, can also be applied to the second through fifth tibial baseplates described herein to illustrate and quantify the above-described differences among the tibial baseplates.

As illustrated in FIGS. 7A-E, a family of tibial baseplate baseplates appropriate for use with the tibial peripheries described herein can be provided. For example, the tibial baseplate illustrated in FIG. 7A can be appropriate for use with the tibial peripheries $T_{1A}$, $T_{1B}$ illustrated in FIGS. 2A-B. The tibial baseplate illustrated in FIG. 7B can be appropriate for use with the tibial peripheries $T_{2A}$, $T_{2B}$ illustrated in FIGS. 3A-B. The tibial baseplate illustrated in FIG. 7C can be appropriate for use with the tibial peripheries $T_{3A}$, $T_{3B}$ illustrated in FIGS. 4A-B. The tibial baseplate illustrated in FIG. 7D can be appropriate for use with the tibial peripheries $T_{4A}$, $T_{4B}$ illustrated in FIGS. 5A-B. The tibial baseplate illustrated in FIG. 7E can be appropriate for use with the tibial peripheries $T_{5A}$, $T_{5B}$ illustrated in FIGS. 6A-B. Within the prosthesis family, a plurality of nominal prosthesis sizes can be provided, with each nominal size having any or all of the five baseplate peripheries described above. Advantageously, this prosthesis family can provide substantial tibial coverage for a wide variety of potential patient tibial geometries.

The above Detailed Description includes references to the accompanying drawings, which form a part of the Detailed Description. The drawings show, by way of illustration, specific embodiments in which the invention can be practiced. These embodiments are also referred to herein as "examples." Such examples can include elements in addition to those shown or described. However, the present inventor also contemplates examples in which only those elements shown or described are provided. Moreover, the present inventor also contemplates examples using any combination or permutation of those elements shown or described (or one or more aspects thereof), either with respect to a particular example (or one or more aspects thereof), or with respect to other examples (or one or more aspects thereof) shown or described herein.

In the event of inconsistent usages between this document and any documents so incorporated by reference, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, device, article, composition, formulation, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

The above Detailed Description is intended to be illustrative, and not restrictive. For example, the above-described examples (or one or more aspects thereof) may be used in combination with each other. Other embodiments can be used, such as by one of ordinary skill in the art upon reviewing the above Detailed Description. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description as examples or embodiments, with each claim standing on its own as a separate embodiment, and it is contemplated that such embodiments can be combined with each other in various combinations or permutations. The scope of the invention should be determined with reference to the appended claims, along with the full scope of equivalents to which such claims are entitled.

The Abstract is provided to comply with 37 C.F.R. §1.72(b), to allow the reader to quickly ascertain the nature of the technical disclosure. It is submitted with the understanding that it will not be used to interpret or limit the scope or meaning of the claims.

What is claimed is:

1. A family of tibial baseplates, comprising:
 a plurality of tibial baseplates and at least one tibial bearing component, each of the tibial baseplates configured to be affixed directly to a tibia and to hold the tibial bearing component, each of the plurality of tibial baseplates defining a common nominal baseplate size, sized to fit the same size patient, each of the plurality of tibial baseplates defining a unique, non-congruent tibial baseplate periphery as compared to the other tibial baseplates of the family of tibial baseplates,
 each of the plurality of tibial baseplates comprising:
  an anteroposterior axis configured to divide the tibial baseplate periphery into a medial compartment and a lateral compartment, the anteroposterior axis configured to be aligned with a home axis when mounted to a resected proximal tibia, the home axis defined as:
   a line segment extending from a posterior point at a geometric center of an attachment area between a posterior cruciate ligament (PCL) and the tibia, to an anterior point disposed on an anterior tubercle of the tibia, the tubercle having a mediolateral width (W), the anterior point disposed on the tubercle at a location medially spaced from a midpoint of the tubercle by an amount equal to about W/6;
  a lateral posterior edge generally opposite an anterior edge of the tibial baseplate periphery and forming a posterior boundary of the lateral compartment, the lateral compartment defining a lateral anteroposterior extent extending from the anterior edge of the tibial baseplate periphery to the lateral posterior edge thereof; and
  a medial posterior edge generally opposite the anterior edge of the tibial baseplate periphery and forming a posterior boundary of the medial compartment, the medial compartment defining a medial anteroposterior extent extending from the anterior edge of the tibial baseplate periphery to the medial posterior edge thereof, wherein the medial anteroposterior extent is larger than the lateral anteroposterior extent; and
  a posterior cruciate ligament (PCL) cutout area generally opposite the anterior edge of the tibial baseplate periphery and between the medial compartment and the lateral compartment, wherein the PCL cutout area is bisected by the anteroposterior axis;

wherein each of the plurality of tibial baseplate peripheries is asymmetrical, wherein each of the plurality of tibial baseplates is configured to provide substantial coverage of a resected proximal tibia surface area and remain within a resected tibial periphery of the resected proximal tibia, wherein each of the plurality of tibial baseplate peripheries is configured to provide a minimal gap between the tibial baseplate periphery and a periphery of a resected proximal tibia, wherein the gap varies in width, and wherein soft tissue edges of the resected proximal tibia have an increased gap width so as to minimize soft tissue impingement upon prosthetic surfaces.

2. The family of tibial baseplates of claim 1, wherein each of the plurality of tibial baseplates comprises a mediolateral extent defining the longest line segment within the tibial baseplate periphery.

3. The family of tibial baseplates of claim 1, wherein the tibial baseplate periphery of each of the plurality of tibial baseplates corresponds to at least one of an asymmetrical tibial periphery, a boxy tibial periphery, a minor asymmetrical tibial periphery, a rounded rectangular tibial periphery, and a rounded square tibial periphery.

4. The family of tibial baseplates of claim 1, wherein each of the plurality of tibial baseplates comprises a chamfer on a medial side.

* * * * *